US005462943A

United States Patent [19]
Seitz et al.

[11] Patent Number: 5,462,943

[45] Date of Patent: Oct. 31, 1995

[54] SUBSTITUTED ACETIC ACID ESTERS USEFUL AS PESTICIDES PER SE AND AS INTERMEDIATES FOR SUBSTITUED ACRYLIC ESTERS PESTICIDES

[75] Inventors: Thomas Seitz, Monheim; Alexander Klausener, Krefeld; Dieter Berg, Wuppertal; Ulrike Wachendorff-Neumann, Monheim; Christoph Erdelen, Leichlingen; Gerd Hänssler, Leverkusen; Wilhelm Brandes, Leichlingen; Stefan Dutzmann, Duesseldorf, all of Germany

[73] Assignee: Bayer Aktiengesellschaft, Leverkusen, Germany

[21] Appl. No.: 89,870

[22] Filed: Jul. 9, 1993

Related U.S. Application Data

[62] Division of Ser. No. 949,903, Sep. 23, 1992, Pat. No. 5,262,416.

[30] Foreign Application Priority Data

Jan. 28, 1990 [DE] Germany .......................... 40 02 466.0

[51] Int. Cl.[6] ...................... A61K 31/505; C07D 403/04; C07D 403/10

[52] U.S. Cl. .......................... 514/256; 544/333; 544/335

[58] Field of Search .................................... 544/298, 299, 544/300, 301, 302, 303, 304, 310, 319, 322, 324, 328, 331, 333, 335; 514/256

[56] References Cited

U.S. PATENT DOCUMENTS 4,812,162 3/1989 Anthony et al. ........................ 544/333

5,091,407 2/1992 de Fraine et al. ...................... 544/333

*Primary Examiner*—Yogendra N. Gupta

*Attorney, Agent, or Firm*—Sprung Horn Kramer & Woods

[57] ABSTRACT

Substituted acetic acid esters of the formula

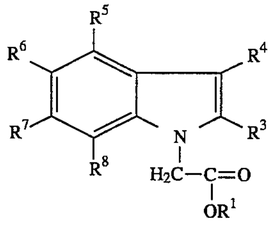

in which $R^1$ Represents alkyl, or represents optionally substituted aralkyl, $R^2$ Represents dialkylamino, alkoxy or alkylthio, or represents in each case optionally substituted aralkyloxy or arylalkylthio, $R^3$ and $R^4$ in each case independently of one another represent hydrogen, cyano, halogen or alkyl, $R^5$, $R^6$ and $R^8$ represent hydrogen or other radicals, and $R^7$ represents optionally substituted pyrimidinyl. The compounds are pesticidially active and also used as intermediates for other acetic acid compounds.

9 Claims, No Drawings

SUBSTITUTED ACETIC ACID ESTERS USEFUL AS PESTICIDES PER SE AND AS INTERMEDIATES FOR SUBSTITUED ACRYLIC ESTERS PESTICIDES

This is a division of application Ser. No. 07/949,903, filed Sep. 23, 1992, now U.S. Pat. No. 5,262,416.

The invention relates to new substituted 2-[6 -(pyrimidinyl)-indol-1-yl]-acrylic esters, to new intermediates and a plurality of processes for their preparation, and to their use as pesticides.

It is known that certain substituted acrylic esters, such as, for example, the compound methyl 3 -methoxy-2-(2-methylphenyl)acrylate, have fungicidal properties (cf., for example, EP-A 178,826).

It is furthermore known that certain alkoxyacrylic esters which are substituted in the 2-position by a 1-indolyl radical, such as, for example, the compound methyl 3-methoxy-2-(indol-1-yl)-acrylate, have fungicidal activity (cf. EP-A 274, 825).

However, the activity of these previously known compounds is not entirely satisfactory in all fields of application, in particular when low amounts and concentrations are applied.

New substituted 2-[6-(pyrimidinyl)-indol-1-yl]-acrylic esters of the general formula (I) have been found

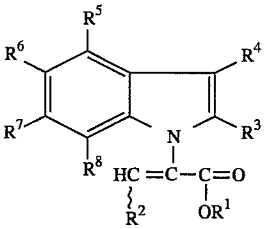

(I)

in which $R^1$represents alkyl, or represents optionally substituted aralkyl, $R^2$represents dialkylamino, alkoxy or alkylthio, or represents in each case optionally substituted aralkyloxy or arylalkylthio, $R^3$ and $R^4$ in each case independently of one another represent hydrogen, cyano, halogen or alkyl, $^5$, Rr$^6$ and $R^8$ independently of one another in each case represent hydrogen, halogen, cyano, nitro, alkyl, alkoxy, alkylthio, halogenoalkyl, halogenoalkoxy, halogenoalkylthio, alkoxycarbonyl, alkoximinoalkyl or cycloalkyl, or represent in each case optionally substituted aryl, aralkyl, aryloxy or arylthio, or in each case optionally substituted hetaryl, hetarylalkyl, hetaryloxy or hetarylthio, or $R^5$ and $R^6$ together represent alkylidenedioxy or alkanediyl, and $R^7$ represents one of the following groups

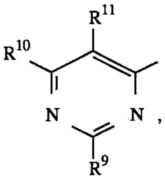,
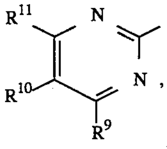,

-continued

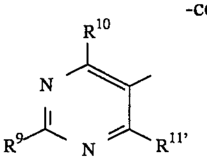
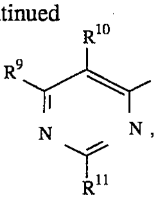,
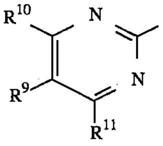

in which $R^9$, $R^{10}$ and $R^{11}$ independently of one another in each case represent hydrogen, halogen, cyano, nitro, alkyl, alkoxy, alkylthio, halogenoalkyl, alkoxycarbonyl, (di)alkylamino or (di)alkylaminocarbonyl, or represent in each case optionally substituted aryl, aralkyl, aryloxy, arylthio, aralkyloxy, aralkylthio, hetaryl, hetaryloxy or hetarylthio, or two adjacent substituents $R^9$ and $R^{10}$, $R^{10}$ and $R^{11}$, or $R^9$ and $R^{11}$, together represent alkanediyl.

The compounds of the formula (I) can be present as geometric isomers or mixtures of isomers of various compositions. The invention extends to the pure isomers as well as the mixtures of isomers.

Furthermore, it has been found that the new substituted 2-[6-(pyrimidinyl)-indol-1-yl]-acrylic esters of the general formula (I)

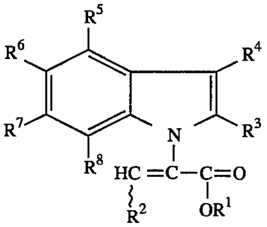

(I)

in which $R^1$, $R^2$, $R^3$, $R^4$, $R^5$, $R^6$, $R^7$ and $R^8$ have the abovementioned meanings, are obtained by one of the processes described below:

a) substituted 2-[6-(pyrimidinyl)-indol-1-yl]-acrylic esters of the general formula (Ia)

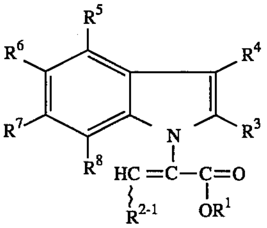

(Ia)

in which $R^1$, $R^3$, $R^4$, $R^5$, $R^6$, $R^7$ and $R^8$ have the abovementioned meanings and $R^{2-1}$ represents alkoxy or unsubstituted or substituted aralkyloxy, are obtained when hydroxyacrylic esters or alkali metal salts thereof of the formula (II)

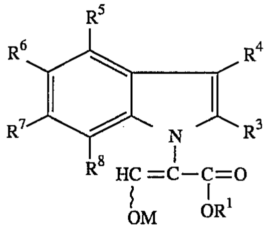
(II)

in which represents hydrogen, or represents an alkali metal cation, and $R^1$, $R^3$, $R^4$, $R^5$, $R^6$, $R^7$ and $R^8$ have the abovementioned meanings, are reacted with alkylating agents of the formula (III)

$R^{12}$—$E^1$ (III)

in which $R^{12}$ represents alkyl or unsubstituted or substituted aralkyl, and $E^1$ represents an electron-attracting leaving group, if appropriate in the presence of a diluent and if appropriate in the presence of a reaction auxiliary;

b) substituted 2-[6-(pyrimidinyl)-indol-1-yl]-acrylic esters of the general formula (Ib)

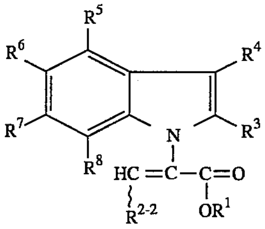
(Ib)

in which $R^1$, $R^3$, $R^4$, $R^5$, $R^6$, $R^7$ and $R^8$ have the abovementioned meanings and $R^{2-2}$ represents dialkylamino, are obtained when substituted acetic esters of the formula (IV)

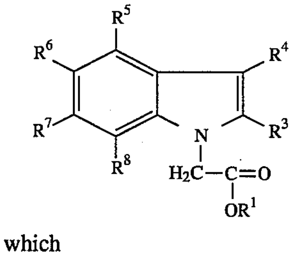
(IV)

in which $R^1$, $R^3$, $R^4$, $R^5$, $R^6$, $R^7$ and $R^8$ have the abovementioned meanings, are reacted with formamides of the formula (Va)

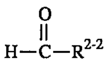
(Va)

in which $R^{2-2}$ has the abovementioned meaning, or with formamide derivatives of the formula (Vb)

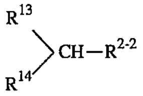
(Vb)

in which $R^{13}$ and $R^{14}$ independently of one another represent alkoxy or dialkylamino and $R^{2-2}$ has the abovementioned meaning, if appropriate in the presence of a diluent;

c) substituted 2-[6-(pyrimidinyl)-indol-1-yl]-acrylic esters of the formula (Ic)

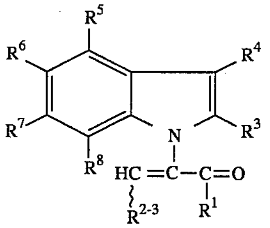
(Ic)

in which $R^1$, $R^3$, $R^4$, $R^5$, $R^6$, $R^7$ and $R^8$ have the abovementioned meanings and $R^{2-3}$ represents alkylthio or unsubstituted or substituted aralkylthio, are obtained when ketocarboxylic acid derivatives of the formula (VI)

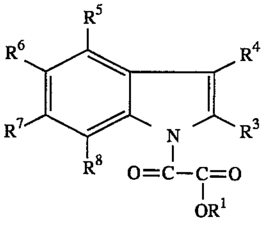
(VI)

in which $R^1$, $R^3$, $R^4$, $R^5$, $R^6$, $R^7$ and $R^8$ have the abovementioned meanings, are reacted with organometallic compounds of the formula (VII)

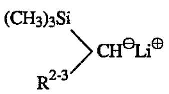
(VII)

in which $R^{2-3}$ has the abovementioned meaning, if appropriate in the presence of a diluent;

d) substituted 2-[6-(pyrimidinyl)-indol-1-yl]-acrylic esters of the formula (Ic) are furthermore obtained when substituted acrylic esters of the formula (VIII)

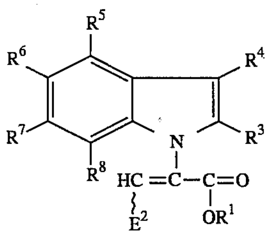

(VIII)

in which $R^1$, $R^3$, $R^4$, $R^5$, $R^6$, $R^7$ and $R^8$ have the abovementioned meanings and $E^2$ represents an electron-attracting leaving group, are reacted with thiols of the formula (IX)

$$R^{2-3}—H \quad (IX)$$

in which $R^{2-3}$ has the abovementioned meaning, if appropriate in the presence of a diluent and if appropriate in the presence of a reaction auxiliary.

Finally, it has been found that the new substituted 2-[6-(pyrimidinyl)-indol-1-yl]-acrylic esters of the general formula (I) have a good action against agricultural pests.

Surprisingly, the substituted 2-[6-(pyrimidinyl)-indol-1-yl]-acrylic esters of the general formula (I) according to the invention have an insecticidal action as well as a considerably better fungicidal activity than the acrylic esters which are known from the prior art and which are compounds of a similar structure and type of action, such as, for example, the compound methyl 3 -methoxy-2-(2-methylphenyl)-acrylate.

Preferred substituents or ranges of the radicals listed in the formulae mentioned above and below are illustrated below:

Alkyl in the definitions of $R^1$, $R^3$, $R^4$, $R^5$, $R^6$, $R^8$, $R^9$, $R^{10}$ and $R^{11}$ in the general formulae represents straight-chain or branched alkyl having preferably 1 to 8, particularly preferably 1 to 6, and in particular 1 to 4, carbon atoms. Examples which may be mentioned are methyl, ethyl, n-propyl, i-propyl, n-butyl, sec-butyl, i-butyl, t-butyl, n-pentyl, i-pentyl, t-pentyl and n-hexyl.

Dialkylamino in the definition of $R^2$ or in compositions such as dialkylaminocarbonyl in the definition of $R^9$, $R^{10}$ and $R^{11}$ represents an amino group having two alkyl groups, each of which can be straight-chain or branched and identical or different, and each of which preferably contains 1 to 6, in particular 1 to 4, carbon atoms, methyl, ethyl and n- and i-propyl being mentioned.

Examples which may be listed are dimethylamino, diethylamino, di-n-propylamino and di-i-propylamino.

The term unsubstituted or substituted aryl in the definition of $R^5$, $R^6$, $R^8$, $R^9$, $R^{10}$ and $R^{11}$ in the general formulae is understood as meaning aryl having preferably 6 to 10 carbon atoms the aryl moiety. Preferred examples which may be mentioned are unsubstituted or substituted phenyl or naphthyl, in particular phenyl.

Unsubstituted or substituted aralkyl in the definitions $R^1$, $R^5$, $R^6$, $R^8$, $R^9$, $R^{10}$ and $R^{11}$ contains preferably 1 to 6, in particular 1 to 4, carbon atoms in the straight-chain or branched alkyl moiety and preferably phenyl as the aryl moiety. Aralkyl groups which may preferably be mentioned as examples are benzyl and phenethyl.

Heteroaryl in the definition of $R^5$, $R^6$, $R^8$, $R^9$, $R^{10}$ and $R^{11}$ generally represents a 5- or 6-membered ring which contains one to four, preferably one to three, identical or different hetero atoms. Hetero atoms which may preferably be mentioned are oxygen, sulphur and nitrogen; the following may preferably be mentioned as examples: pyrimidinyl, pyrrolyl, isothiazolyl, oxazolyl, pyridyl, thienyl, furyl, pyridazinyl, pyrazinyl, isoxazolyl, thiazolyl and pyrazolyl.

The term alkoxy in the definition of $R^2$, $R^5$, $R^6$, $R^8$, $R^9$, $R^{10}$ and $R^{11}$ in the general formulae is understood as meaning straight-chain or branched alkoxy having preferably 1 to 6, in particular 1 to 4, carbon atoms. Examples which may be mentioned are methoxy, ethoxy, propoxy, butoxy as well as their isomers, i-propoxy and i-, s- and t-butoxy.

Halogen in the definitions of $R^3$, $R^4$, $R^5$, $R^6$, $R^8$, $R^9$, $R^{10}$ and $R^{11}$ represents fluorine, chlorine, bromine and iodine, preferably fluorine, chlorine and bromine, and particularly preferably fluorine and chlorine.

Alkyl in radicals such as alkoximinoalkyl the definitions of $R^5$, $R^6$ and $R^8$ represents straight-chain or branched alkyl, preferably having 1 to 6, particularly preferably having 1 to 4, carbon atoms with methyl, ethyl and t-butyl being very particularly preferred. The exemplary enumeration corresponds to that given further above.

Alkylthio in the definitions of $R^2$, $R^5$, $R^6$, $R^8$, $R^9$, $R^{10}$ and $R^{11}$ represents straight-chain or branched alkylthio having preferably 1 to 6 carbon atoms, for example it is understood as meaning the following groups: methylthio-, ethylthio-, propylthio-, butylthio-, pentylthio as well as their isomers, such as, for example, i-propylthio, i-, s- and t-butylthio, 1-methyl-butylthio, 2 -methyl-butylthio- and 3-methyl-butylthio. Preferred alkylthio radicals contain 1 to 4 carbon atoms. ,Methylthio, ethylthio, n-, i-, s-propylthio and n-, i-, s- and t-butylthio are particularly preferred.

Halogenoalkyl and halogenoalkoxy in the definitions of $R^5$, $R^6$, $R^8$, $R^9$, $R^{10}$ and $R^{11}$ represent straight-chain or branched halogenoalkyl or halogenoalkoxy each of which has 1 to 4 carbon atoms, particularly preferably 1 or 2 carbon atoms, and in each case 1 to 9, preferably 1 to 5, identical or different halogen atoms as defined under halogen; the following may be mentioned by way of example: fluoromethyl, chloromethyl, bromomethyl, fluoroethyl, chloroethyl, bromomethyl, fluoro-n-propyl, chloro-n-propyl, difluoromethyl, trifluoromethyl, dichloromethyl, trichloromethyl, difluoroethyl, trifluoroethyl, trichloroethyl, chlorodifluoro-methyl, trifluorochloroethyl, chlorobutyl, fluorobutyl, fluoromethoxy, chloromethoxy, bromomethoxy, fluoroethoxy, chloroethoxy, bromoethoxy, fluoropropoxy, chloropropoxy, bromopropoxy, fluorobutoxy, chlorobutoxy, fluoro-i-propoxy, chloro-i-propoxy, difluoromethoxy, trifluoromethoxy, dichloromethoxy, trichloromethoxy, difluoroethoxy, trifluoroethoxy, tetrafluoroethoxy, trichloroethoxy, chlorodifluoromethoxy and trifluorochloroethoxy.

Halogenoalkylthio in the definitions of $R^5$, $R^6$ and $R^8$ represents straight-chain or branched halogenoalkylthio each of which has 1 to 4 carbon atoms, particularly preferably 1 or 2 carbon atoms, and in each case 1 to 9, preferably 1 to 5, identical or different halogen atoms as defined under halogen; the following may be mentioned by way of example: fluoromethylthio, chloromethylthio, bromomethylthio, fluoroethylthio, chloroethylthio, bromomethylthio, fluoropropylthio, chloropropylthio, bromopropylthio, fluorobutylthio, chlorobutylthio, bromobutylthio, fluoro-i-propylthio, chloro-i-propylthio, difluoromethylthio, trifluoromethylthio, dichloromethylthio, trichloromethylthio, difluoroethylthio, trifluoroethylthio, tetrafluoroethylthio, trichloroethylthio, chlorodifluoromethylthio and trifluorochloroethylthio.

Alkoxycarbonyl in the definitions $R^5$, $R^6$, $R^8$, $R^9$, $R^{10}$ and $R^{11}$ represents straight-chain or branched alkoxycarbonyl having 1 to 4, preferably 1 or 2, carbon atoms in the alkoxy radical; the following may be mentioned by way of example: methoxycarbonyl, ethoxycarbonyl, n-propoxycarbonyl, i-propoxycarbonyl, n-, i-, s- and t-butoxycarbonyl.

Cycloalkyl in the definitions of $R^5$, $R^6$ and $R^8$ represents cycloalkyl having preferably 3 to 7, in particular 3, 5 or 6, carbon atoms. Examples which may be mentioned are unsubstituted or substituted cyclopropyl, cyclobutyl, cyclopentyl, cyclohexyl and cycloheptyl.

Unsubstituted or substituted aryloxy and arylthio in the definitions of $R^5$, $R^6$, $R^8$ and $R^9$ in the general formulae represent aryl having preferably 6 to 10 carbon atoms in the aryl moiety. Examples which may be mentioned are unsubstituted or substituted phenyl or naphthyl, phenoxy or phenylthio, in particular phenyl.

Unsubstituted or substituted aralkyloxy or aralkylthio in the definitions of $R^2$, $R^5$, $R^6$, $R^8$, $R^9$, $R^{10}$ and $R^{11}$ preferably contain 1 to 6 carbon atoms in the straight-chain or branched alkyl moiety and preferably phenyl as the aryl moiety. Alkyl groups which may be mentioned by way of example are benzyl, phenethyl, benzyloxy and benzylthio.

Hetarylalkyl, hetaryloxy and hetarylthio in the definition of $R^5$, $R^6$, $R^8$, $R^9$, $R^{10}$ and $R^{11}$ generally represent a 5- to 6-membered ring which contains one or more hetero atoms, preferably 1 to 3 identical or different hetero atoms. Hetero atoms which may preferably be mentioned are oxygen, sulphur and nitrogen; the following may be mentioned by way of example: pyridyl, thienyl, furyl, pyridazinyl, pyrazinyl, isoxazolyl, thiazolyl, pyridylmethyl, thienylmethyl, furylmethyl, pyridyloxy, thienyloxy, furyloxy, pyridazinyloxy, pyrazinyloxy, isoxazolyloxy, thiazolyloxy, pyridylmethyloxy, thienylmethyloxy, furylmethyloxy, pyridylthio, thienylthio, furylthio, pyridazinylthio, pyrazinylthio, isoxazolylthio, thiazolylthio, pyridylmethylthio, thienylmethylthio and furylmethylthio.

The substituents for the aryl radicals as such or in radicals such as arylalkyl, aryloxy, arylthio or aralkyloxy, and for the heterocyclic rings such as hetarylalkyl and hetaryl, have the meanings given below.

Halogen as a substituent generally represents fluorine, chlorine, bromine and iodine, preferably fluorine, chlorine and bromine, particularly preferably fluorine and chlorine.

Alkyl as a substituent or in radicals such as alkoximinoalkyl generally represents straight-chain or branched alkyl, preferably having 1 to 6, particularly preferably 1 to 4, carbon atoms with methyl, ethyl, i-propyl and t-butyl being very particularly preferred. The exemplary enumeration corresponds to that given further above.

Alkoxy as a substituent or in radicals such as alkoximinoalkyl generally represents straight-chain or branched alkoxy having 1 to 6, particularly preferably 1 to 3, carbon atoms per alkyl radical; preferred examples which may be mentioned are: methoxy, ethoxy, n- and i-propoxy, n-, i-, s- and t-butoxy and n-hexoxy and i-hexoxy.

Alkylthio as a substituent in the radicals generally represents straight-chain or branched alkylthio having preferably 1 to 6 carbon atoms; for example it is understood as meaning the following groups: methylthio-, ethylthio-, propylthio-, butylthio-, pentylthio as well as their isomers, such as, for example, i-propylthio, i-, s- and t-butylthio, 1-methyl-butylthio, 2 -methyl-butylthio- and 3-methyl-butylthio. Preferred alkylthio radicals contain 1 to 4 carbon atoms. Methylthio, ethylthio, n-, i-, s-propylthio and n-, i-, s- and t-butylthio are particularly preferred.

Halogenoalkyl and halogenoalkoxy as substituents in the radicals generally represent straight-chain or branched halogenoalkyl or halogenoalkoxyeach having 1 to 4 carbon atoms, particularly preferably 1 or 2 carbon atoms, and in each case 1 to 9, preferably 1 to 5, identical or different halogen atoms as defined under halogen; the following may be mentioned by way of example: fluoromethyl, chloromethyl, bromomethyl, fluoroethyl, chloroethyl, bromomethyl, fluoro-n-propyl, chloro-n-propyl, difluoromethyl, tifluoromethyl, dichloromethyl, trichloromethyl, difluoroethyl, trifluoroethyl, trichloroethyl, chloro-difluoro-methyl, trifluorochloroethyl, chlorobutyl, fluorobutyl, fluoromethoxy, chloromethoxy, bromomethoxy, fluoroethoxy, chloroethoxy, bromoethoxy, fluoropropoxy, chloropropoxy, bromopropoxy, fluorobutoxy, chlorobutoxy, fluoro-i-propoxy, chloro-i-propoxy, difluoromethoxy, trifluoromethoxy, dichloromethoxy, trichloromethoxy, difluoroethoxy, trifluoroethoxy, tetrafluoroethoxy, trichloroethoxy, chlorodifluoromethoxy and trifluorochloroethoxy.

Halogenoalkylthio as a substituent in the radicals generally represents straight-chain or branched halogenoalkylthio in each case having 1 to 4 carbon atoms, particularly preferably 1 or 2 carbon atoms, and in each case 1 to 9, preferably 1 to 5, identical or different halogen atoms as defined under halogen; examples which may be mentioned are: fluoromethylthio, chloromethylthio, bromomethylthio, fluoroethylthio, chloroethylthio, bromomethylthio, fluoropropylthio, chloropropylthio, bromopropylthio, fluorobutylthio, chlorobutylthio, bromobutylthio, fluoro-i-propylthio, chloro-i-propylthio, difluoromethylthio, trifluoromethylthio, dichloromethylthio, trichloromethylthio, difluoroethylthio, trifluoroethylthio, tetrafluoroethylthio, trichloroethylthio, chlorodifluoromethylthio and trifluorochloroethylthio.

The definitions mentioned here are also true in an analogous manner for the preferred combinations of radicals which are listed below.

Formula (I) provides general definition of the new substituted 2-[6-(pyrimidinyl)-indol-1-yl]-acrylic esters according to the invention. Preferred compounds of the formula (I) are those in which $R^1$ represents straight-chain or branched alkyl having 1 to 6 carbon atoms, or represents benzyl, $R^2$represents dialkylamino having in each case 1 to 6 carbon atoms in the individual straight-chain or branched alkyl moieties, in each case straight-chain or branched alkoxy or alkylthio having 1 to 6 carbon atoms, or represents benzyloxy or benzylthio, each of which is optionally monosubstituted or polysubstituted by identical or different substituents, suitable phenyl substituents being: halogen, in each case straight-chain or branched alkyl, alkoxy or alkylthio each having 1 to 4 carbon atoms, in each case straight-chain or branched halogenoalkyl, halogenoalkoxy or halogenoalkylthio each having 1 to 4 carbon atoms and 1 to 9 identical or different halogen atoms, or cycloalkyl having 3 to 7 carbon atoms, $R^3$ and $R^4$ in each case independently of one another represent hydrogen, cyano, fluorine, chlorine, bromine or straight-chain or branched alkyl having 1 to 6 carbon atoms, $R^5$, $^6$ and $R^8$ independently of one another in each case represent hydrogen, fluorine, chlorine, bromine, cyano, nitro, in each case straight-chain or branched alkyl, alkoxy or alkylthio each of which has 1 to 4 carbon atoms, in each case straight-chain or branched halogenoalkyl, halogenoalkyl or halogenoalkylthio, each of which has 1 to 4 carbon atoms and 1 to 9 identical or different halogen atoms, in each case straight-chain or branched alkoxycarbonyl or alkoximinoalkyl each of which has 1 to 4 carbon atoms in the individual alkyl moieties, cycloalkyl having 3 to 7 carbon atoms, or represent phenyl, benzyl, phenoxy, phenylthio, benzyloxy or benzylthio, each of which is unsubstituted or monosubstituted to trisubstituted in the aryl moiety by identical or different substituents from the series comprising fluorine, chlorine, bromine, alkyl, alkoxy, alkylthio, halogenoalkyl, halogenoalkoxy or halogenoalkylthio each of which has 1 to 4 carbon atoms and if appropriate 1 to 9 identical or different halogen atoms, or represent pyridyl, thienyl, furyl, pyridazinyl, pyrazinyl, thiazolyl, pyridylmethyl, thienylmethyl, furylmethyl, pyridyloxy, thienyloxy, thiazolyloxy, pyridylmethyloxy, thienylmethyloxy, thienylthio, furylthio, pyridylmethylthio or thienylmethylthio each of which is optionally monosubstituted or disubstituted in the heteroaryl moiety by identical or different substituents from the series comprising halogen, alkyl, alkoxy, alkylthio, halogenoalkyl, halogenoalkoxy or halogenoalkylthio each of which has 1 to 4 carbon atoms and if appropriate 1 to 9 identical or different halogen atoms, or $R^5$ and $R^6$ together represent alkanediyl having 3 to 5 carbon atoms, or represent alkylidenedioxy having 1 to 3 carbon atoms, and $R^7$ represents one of the following groups

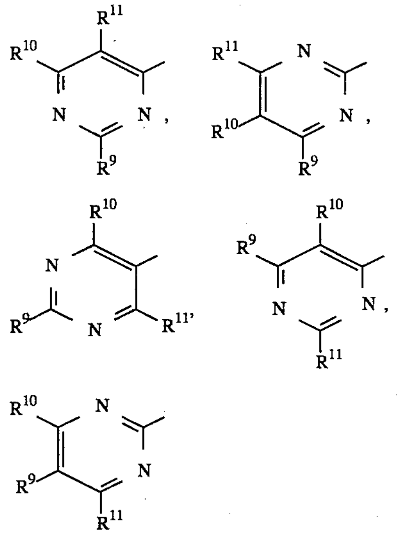

where $R^9$, $R^{10}$ and $R^{11}$ in each case independently of one another represent hydrogen, fluorine, chlorine, bromine, cyano, in each case straight-chain or branched alkyl, alkoxy, alkylthio or halogenoalkyl having 1 to 6 carbon atoms and if appropriate 1 to 13 identical or different halogen atoms, or represent cycloalkyl having 3 to 7 carbon atoms, or represent straight-chain or branched alkoxycarbonyl having 1 to 6 carbon atoms, or represent dialkylaminocarbonyl, alkylaminocarbonyl, dialkylamino or alkylamino, each of which has 1 to 4 carbon atoms, each of which is straight-chain or branched in the individual alkyl moieties and each of which is optionally substituted by identical or different substituents, or represents phenyl, benzyl, phenyloxy, phenylthio, benzyloxy or benzylthio, each of which is unsubstituted or monosubstituted to trisubstituted by identical or different substituents, or represents pyrrolyl, thienyl, furyl, thiazolyl, isothiazolyl, oxazolyl, isoxazolyl, pyrazolyl, imidazolyl, pyridyl, pyrimidyl, pyridazinyl, pyrazinyl, triazinyl, pyrrolyloxy, thienyloxy, furyloxy, thiazolyloxy, isothiazolyloxy, oxazolyloxy, isoxazolyloxy, pyrazolyloxy, imidazolyloxy, pyridyloxy, pyrimidyloxy, pyridazinyloxy, pyrazinyloxy, pyrrolylthio, thienylthio, furylthio, thiazolylthio, isothizolythio, oxazolylthio, isoxazolylthio, pyrazolylthio, imidazolylthio, pyridylthio, pyrimidylthio, pyridazinylthio or pyrazinylthio, each of which is unsubstituted or monosubstituted or disubstituted by identical or different substituents, suitable substituents in each case being: halogen, in each case straight-chain or branched alkyl, alkoxy, alkylthio, halogenoalkyl, halogenoalkoxy or halogenoalkylthio each of which has 1 to 4 carbon atoms and, if appropriate, in each case 1 to 9 identical or different halogen atoms, alkylcarbonylamino having 1 to 4 carbon atoms in the straight-chain or branched alkyl moiety, dialkylamino or dialkylaminocarbonyl each of which has 1 to 4 carbon atoms in the respective straight-chain or branched alkyl moieties, and in each case optionally substituted phenyl or benzyl, or two adjacent substituents $R^9$ and $R^{10}$, or $R^{10}$ and $R^{11}$, $R^9$ and $R^{11}$, together represent alkanediyl having 3 or 4 carbon atoms.

Particularly preferred compounds of the formula (I) are those in which $R^1$ represents straight-chain or branched alkyl having 1 to 4 carbon atoms, $R^2$ represents dialkylamino having in each case 1 to 4 carbon atoms in the respective straight-chain or branched alkyl moieties, or represents in each case straight-chain or branched alkoxy or alkylthio having 1 to 4 carbon atoms, or represents benzyloxy or benzylthio, $R^3$ and $R^4$ are identical or different and represent hydrogen, cyano, fluorine, chlorine, bromine, methyl, ethyl, n- or i-propyl or n-, i-, s- or t-butyl, $R^5$ and $R^6$ are identical or different and represent hydrogen, fluorine, chlorine, bromine, cyano, nitro, methyl, ethyl, n- or i-propyl, n-, i-, s-_ or t-butyl, methoxy, ethoxy, n- or i-propoxy, methylthio, trifluoromethyl, trifluoromethoxy, difluoromethoxy, trifluoromethylthio, methoxycarbonyl, ethoxycarbonyl, methoximinomethyl, ethoximinomethyl, methoximinoethyl, ethoximinoethyl, cyclopentyl or cyclohexyl, or $R^5$ and $R^6$ together represent a methylenedioxy, 1,3-propanediyl or 1,4-butanediyl group, $R^7$ represents one of the following groups

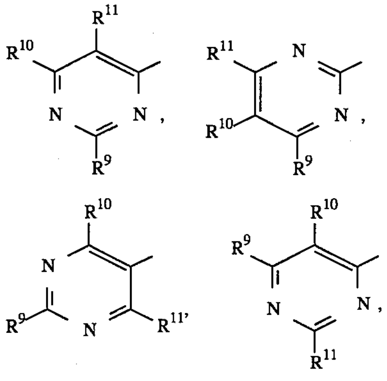

-continued

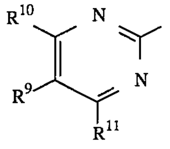

where $R^9$ represents hydrogen, in each case straight-chain or branched alkyl, alkoxy or alkylthio each of which has 1 to 6 carbon atoms, cyclopentyl, cyclohexyl, methylamino, ethylamino, dimethylamino, diethylamino, or represents phenyl, benzyl, phenoxy, phenylthio, benzyloxy or benzylthio each of which is optionally monosubstituted to trisubstituted by identical or different substituents, or represents pyrrolyl, thienyl, furyl, thiazolyl, isothiazolyl, oxazolyl, isoxazolyl, pyrazolyl, imidazolyl, triazinyl, pyridyl, pyrimidyl, pyridazinyl, pyraziyl, pyridylmethyl, thienylmethyl, furylmethyl, pyridyloxy, thienyloxy, thiazolyloxy, pyridylmethyloxy, thienylmethyloxy, thienylthio, furylthio, pyridylmethylthio or thienylmethylthio each of which is optionally monosubstituted or disubstituted by identical or different substituents, suitable substituents in each case being halogen, methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylcarbonylamino, ethylcarbonylamino, methylcarbonyl, ethylcarbonyl, n- or i-propylcarbonyl, n-, i-, s- or t-butylcarbonyl or halogenoalkyl, halogenoalkoxyor halogenoalkylthio each of which has 1 or 2 carbon atoms and 1 to 5 identical or different fluorine or chlorine atoms, dialkylamino or dialkylaminocarbonyl having 1 or 2 carbon atoms in the individual alkyl moieties, or phenyl or benzyl each of which are unsubstituted or mono-substituted to disubstituted by identical or different substituents, suitable phenyl or benzyl substituents in each case being fluorine, chlorine, methyl, methoxy or phenoxy, and $R^{10}$ and $R^{11}$ are identical or different and represent hydrogen, straight-chain or branched alkyl having 1 to 4 carbon atoms, chlorine, bromine, cyano, methoxycarbonyl, ethoxycarbonyl, dimethylaminocarbonyl, dithylaminocarbonyl, methylaminocarbonyl, ethylaminocarbonyl, methoxy, ethoxy, methylthio or ethylthio, or $R^{10}$ and $R^{11}$ together represent a methylenedioxy, 1,3 -propanediyl or 1,4-butanediyl group, and $R^8$ represents hydrogen, fluorine, chlorine, bromine, methyl, ethyl, n- or i-propyl, methoxy, ethoxy, n- or i-propoxy, methylthio, trifluoromethyl, trifluoromethoxy, difluoromethoxy, trifluoromethylthio, methoxycarbonyl, ethoxycarbonyl, methoximinomethyl or ethoximinomethyl.

Very particularly preferred compounds of the formula (I) are those in which $R^1$ represents methyl or ethyl, $R^2$ represents dimethylamino, diethylamino, methoxy, ethoxy, methylthio, ethylthio, benzyloxy or benzylthio, $R^3$represents hydrogen, chlorine or methyl, $R^4$ represents hydrogen, chlorine or methyl, $R^5$ represents hydrogen, fluorine, chlorine, bromine, methyl, ethyl, trifluoromethyl, methoxycarbonyl or ethoxycarbonyl, $R^6$ represents hydrogen, fluorine, chlorine, bromine, methyl, ethyl, methoxy, ethoxy, methylthio, trifluoromethyl, methoxycarbonyl or ethoxycarbonyl, or $R^5$ and $R^6$ together represent a methylenedioxy, 1,3-propanediyl or 1,4-butanediyl group, $R^7$ represents one of the following groups

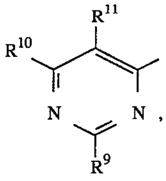 ,

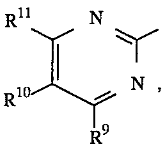 ,

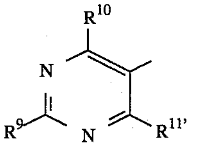

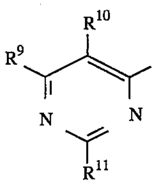 or

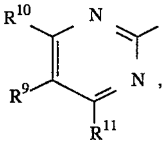 , where $R^9$represents hydrogen, methyl, ethyl, n- or i-propyl, n-, s-, i- or t-butyl, n- or i-amyl, n-hexyl, methoxy, ethoxy, n- or i-propoxy, methylthio, ethylthio, n- or i-propylthio, cyclohexyl, methylamino, ethylamino, dimethylamino, diethylamino, benzyl, o-, m- or p-chlorobenzyl, o-, m- or p-methylbenzyl, phenyl which is optionally monosubstituted to trisubstitited by identical or different substituents, pyridyl, thienyl, furyl, pyrimidinyl, pyridazinyl, pyrazinyl or thiazolyl, each of which is optionally monosubstituted or disubstituted by identical or different substituents, suitable substituents in each case being fluorine, chlorine, methyl, ethyl, t-butyl, methoxy, ethoxy, methylthio, methylcarbonylamino, methylcarbonyl, ethylcarbonyl, trifluoromethyl, trifluoromethoxy, trifluoromethylthio, 1,3-propanediyl, phenyl, p-chlorophenyl, m- or p-pheoxyphenyl or benzyl, and $R^{10}$ and $R^{11}$ independently of one another represent hydrogen, methyl, ethyl, chlorine, bromine, methoxycarbonyl or ethoxycarbonyl, or $R^{10}$ and $R^{11}$ together represent a methylenedioxy, 1,3 -propanediyl or 1,4-butanediyl group, and $R^8$ represents hydrogen, methyl or ethyl.

The following substituted 2-[6-(pyrimidinyl)-indol- 1-yl] -acrylic esters of the general formula (I) may be mentioned individually in addition to the compounds mentioned in the preparation examples:

TABLE 1
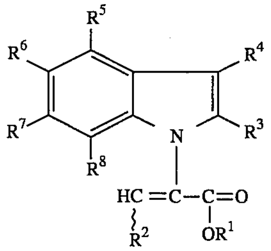
(I)
| $R^1$ | $R^2$ | $R^3$ | $R^4$ | $R^5$ | $R^6$ | $R^7$ | $R^8$ |
|---|---|---|---|---|---|---|---|
| $CH_3$ | $-OCH_3$ | H | H | H | H | 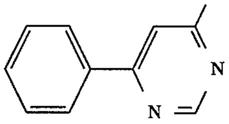 | H |
| $CH_3$ | $-N(CH_3)_2$ | H | H | H | H | 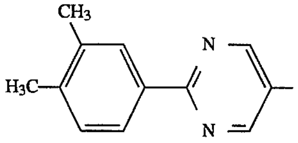 | H |
| $CH_3$ | $-SCH_3$ | H | H | H | H | 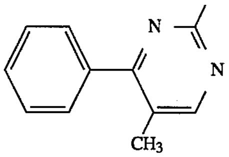 | H |
| $CH_3$ | $-OCH_3$ | H | H | H | H | 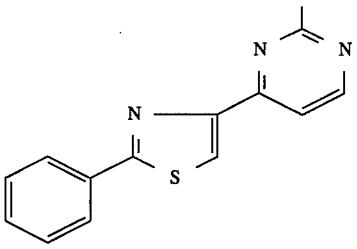 | H |
| $CH_3$ | $-OCH_3$ | H | H | H | H | 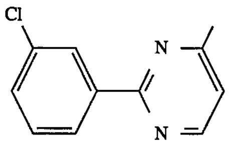 | H |
| $CH_3$ | $-OCH_3$ | H | H | H | H | 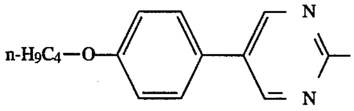 | H |
| $CH_3$ | $-OCH_3$ | H | H | H | H | 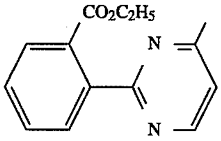 | H |
| $CH_3$ | $-OCH_3$ | H | H | H | H | 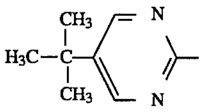 | H |

TABLE 1-continued
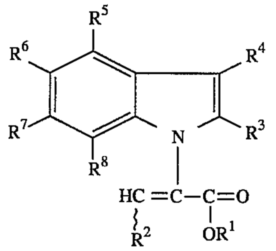
(I)
| $R^1$ | $R^2$ | $R^3$ | $R^4$ | $R^5$ | $R^6$ | $R^7$ | $R^8$ |
|---|---|---|---|---|---|---|---|
| $CH_3$ | $-OCH_3$ | H | H | H | H | 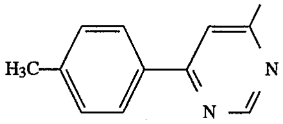 | H |
| $CH_3$ | $-OCH_3$ | H | H | H | H | 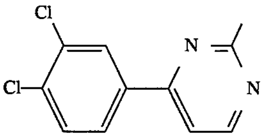 | H |
| $CH_3$ | $-OCH_3$ | H | H | H | H | 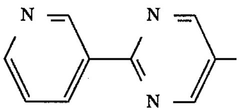 | H |
| $CH_3$ | $-OCH_3$ | H | H | H | H | 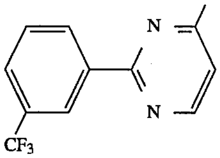 | H |
| $CH_3$ | $-OCH_3$ | H | H | H | H | 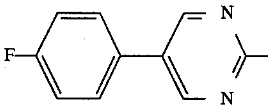 | H |
| $CH_3$ | $-OCH_3$ | H | H | H | H | 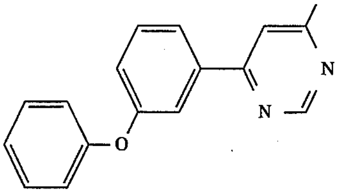 | H |
| $CH_3$ | $-OCH_3$ | H | H | H | H | 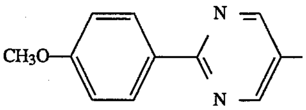 | H |
| $CH_3$ | $-OCH_3$ | H | H | H | H | 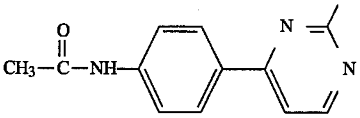 | H |
| $CH_3$ | $-OCH_3$ | H | H | H | H | 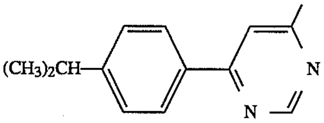 | H |

TABLE 1-continued

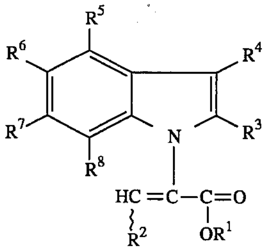

(I)

| $R^1$ | $R^2$ | $R^3$ | $R^4$ | $R^5$ | $R^6$ | $R^7$ | $R^8$ |
|---|---|---|---|---|---|---|---|
| $CH_3$ | $-OCH_3$ | H | H | H | H | 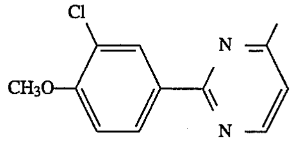 | H |

If, for example, methyl 3-hydroxy-2-[6-[4 -(phenyl)-pyrimidin-2-yl]-indol-1-yl]-acrylate and dimethyl sulphate are used as starting substances, the course of the reaction of process (a) according to the invention may be represented by the following equation:

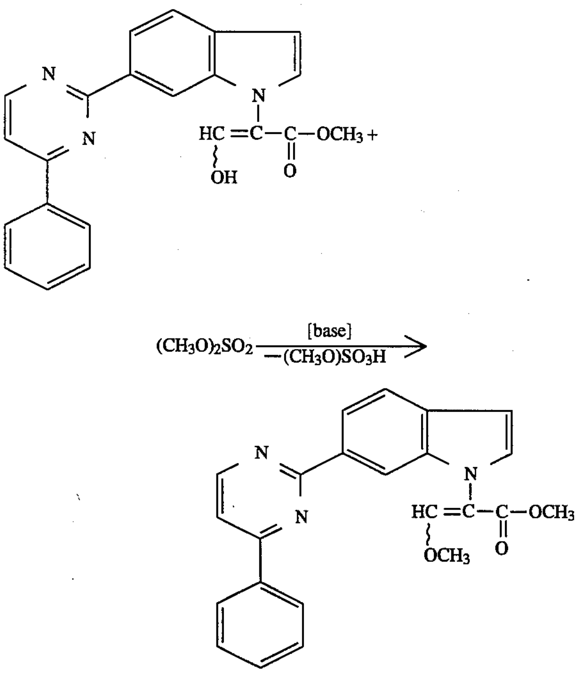

If, for example, methyl [6-[4-(phenyl)-pyrimidin-2-yl]-indol-1-yl]-acetate and dimethylformamide dimethyl acetal are used as starting substances, the course of the reaction of process (b) according to the invention may be represented by the following equation:

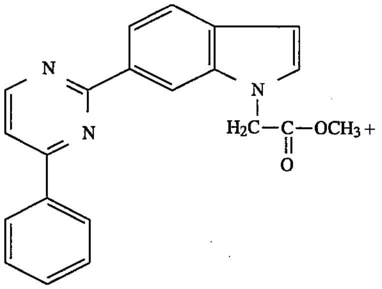

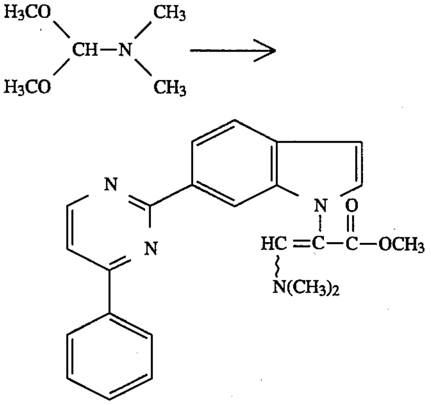

If, for example, methyl 2-oxo-2-[6-(4-(phenyl)-pyrimidin-2-yl]-indol-1-yl]-acetate and [(methylthio)(trimethylsilyl)]-methylene-lithium are used as starting compounds, the course of the reaction of process (c) according to the invention may be represented by the following equation:

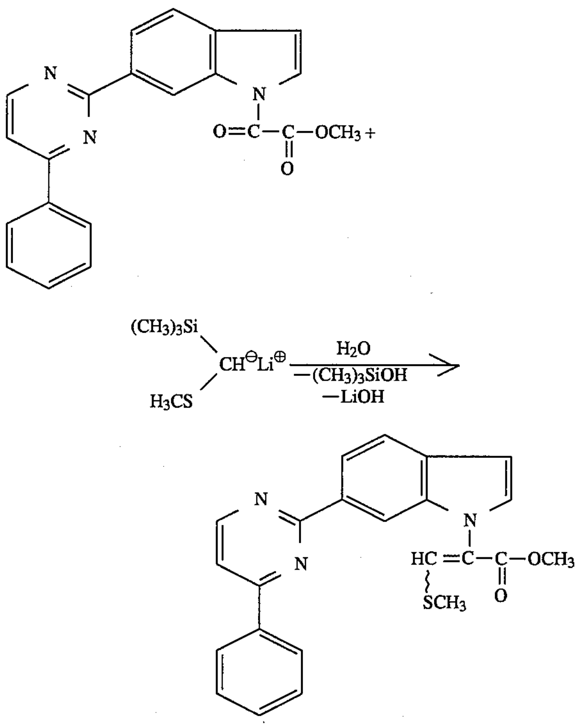

If, for example, methyl 2-[6-[4-(4-methylphenyl)pyrimidin-2-yl]-indol-1-yl]-3-methanesulphonyloxy-acrylate and methanethiol are used as starting substances, process (d) according to the invention may be represented by the following equation:

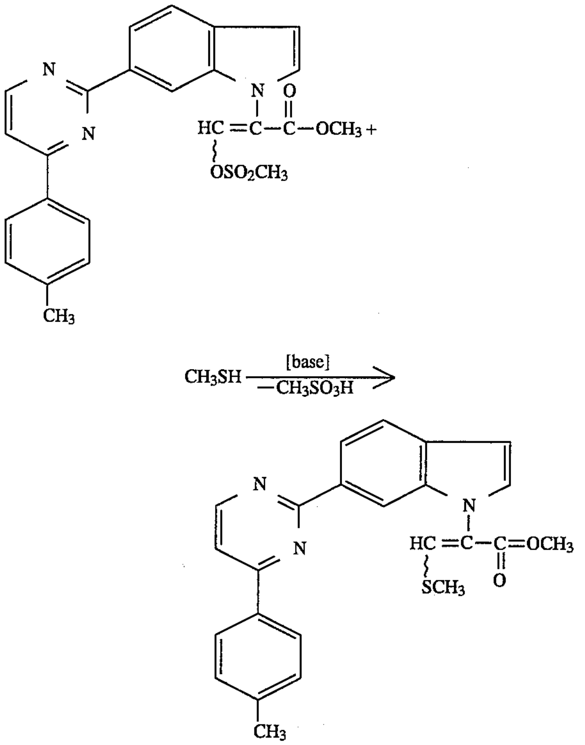

Formula (II) provides a general definition of the hydroxyacrylic esters or their alkali metal salts which are required as starting substances for carrying out process (a) according to the invention. In this formula (II) $R^1$, $R^3$, $R^4$, $R^5$, $R^6$, $R^7$, and $R^8$ preferably represent those radicals which have already been mentioned in connection with the description of the substances of the formula (I) according to the invention as being preferred for these substituents. M preferably represents hydrogen, or represents a lithium, sodium or potassium cation.

The hydroxyacrylic esters of the formula (II) required for carrying out process (a) according to the invention were hitherto unknown and are a subject of the invention.

They are obtained when substituted acetic esters of the formula (IV)

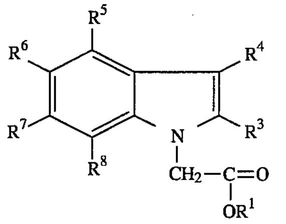

(IV)

in which $R^1$, $R^3$, $R^4$, $R^5$, $R^6$, $R^7$ and $R^8$ have the abovementioned meanings, are reacted with formic esters of the formula (X)

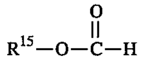

(X)

in which $R^{15}$ represents alkyl, in particular methyl or ethyl, if appropriate in the presence of a diluent such as, for example, dimethylformamide, and if appropriate in the presence of a basic reaction auxiliary such as, for example, sodium hydride, at temperatures of from −20° C. to +50° C. (cf., for example, EP-A 274,825).

Formic esters of the formula (X) are generally known compounds of organic chemistry.

Formula (III) provides a general definition of the alkylating agents furthermore required as starting substances for carrying out process (a) according to the invention. In this formula (III), $R^{12}$ preferably represents those radicals which have already been mentioned in connection with the description of the substances of the formula (I) according to the invention as being preferred for this substituent.

$E^1$ represents a leaving group customary in alkylating agents, preferably an optionally substituted alkyl, alkoxy or arylsulphonyloxy radical such as, for example, a methoxysulphonyloxy radical, an ethoxysulphonyloxy radical or a p-toluenesulphonyloxy radical, or represents halogen, in particular chlorine, bromine or iodine.

The alkylating agents of the formula (III) are generally known compounds of organic chemistry.

The substituted acetic esters of the general formula (IV) which are required as starting substances for carrying out process (b) according to the invention and for the synthesis of the precursors of the formula (II) are new and likewise a subject of the invention. In this formula $R^1$, $R^3$, $R^4$, $R^5$, $R^6$, $R^7$ and $R^8$ preferably represent those radicals which have already been mentioned in connection with the description of the substances of the formula (I) according to the invention as being preferred for these substituents. The substituted acetic esters of the general formula (IV) are likewise effective as plant protection agents and are also claimed with a view to their biological use.

The compounds of the formula (IV) are obtained when indole derivatives of the general formula (XI)

(XI)

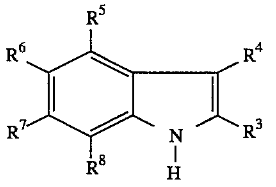

in which $R^3$, $R^4$, $R^5$, $R^6$, $R^7$ and $R^8$ have the abovementioned meanings, are reacted with acetic acid derivatives of the general formula (XII)

$$E^3—CH_2—COOR^1 \quad (XII)$$

in which $R^1$ has the abovementioned meaning and $E^3$ represents an electron-attracting leaving group, preferably halogen, in particular chlorine or bromine, if appropriate in the presence of a diluent such as, for example, acetonitrile or acetone, and if appropriate in the presence of a basic auxiliary such as, for example, potassium carbonate or potassium tert.-butylate, at temperatures of between −20° C. and +100° C.

The acetic acid derivatives of the formula (XII) are generally known compounds of organic chemistry.

The indole derivatives of the general formula (XI) were hitherto unknown and are a subject of the invention. However, they are obtained by known processes in an analogous manner, for example by reacting nitrobenzene derivatives of the formula (XIII)

(XIII)

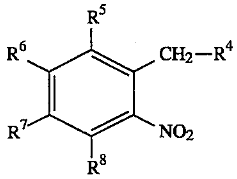

in which $R^4$, $R^5$, $R^6$, $R^7$ and $R^8$ have the abovementioned meanings, with compounds of the formula (XIV)

(XIV)

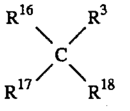

in which $R^3$ has the abovementioned meaning, $R^{16}$ represents alkoxy or dialkylamino, $R^{17}$ represents alkoxy or dialkylamino and $R^{18}$ represents dialkylamino, if appropriate in the presence of a diluent such as, for example, toluene or dimethylformamide, at temperatures between 25° C. and 200° C., and if appropriate under a pressure of 1 to 100 bar, to give the compounds of the general formula (XV)

(XV)

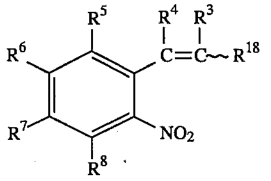

in which $R^3$, $R^4$, $R^5$, $R^6$, $R^7$, $R^8$ and $R^{18}$ have the abovementioned meanings, and the resulting compounds of the formula (XV) may then be isolated and/or purified and are then cyclized using customary reducing agents such as, for example, hydrogen, in the presence of a suitable catalyst such as, for example, Raney nickel, and at a pressure between 1 and 200 bar at temperatures between −20° C. and +200° C., if appropriate in the presence of a diluent such as, for example, methanol, ethanol, tetrahydrofuran or dioxane, and if appropriate in the presence of an inert gas such as, for example, nitrogen.

The compounds of the formula (XV) are new and likewise a subject of the invention.

The compounds of the general formula (XIV) are generally known compounds of organic chemistry (cf. Tetrahedron 35, 1675 (1979)).

The nitrobenzene derivatives of the formula (XIII)

(XIII)

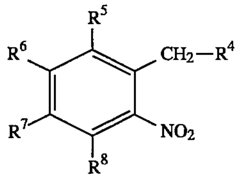

in which $R^4$, $R^5$, $R^6$, $R^7$ and $R^8$ have the abovementioned meanings are new.

The nitrobenzene derivatives of the formula (XIII) are obtained by one of the processes described below:

a) Nitrobenzene derivatives of the general formula (XIII-a)

(XIII-a)

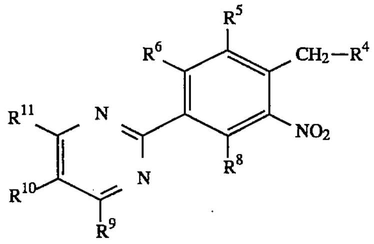

in which $R^4$, $R^5$, $R^6$, $R^8$, $R^9$, $R^{10}$ and $R^{11}$ have the abovementioned meanings, are obtained when compounds of the formula (XVI)

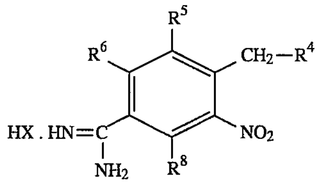

(XVI)

in which $R^4$, $R^5$, $R^6$ and $R^8$ have the abovementioned meanings and

HX represents the equivalent of an inorganic acid such as, for example, hydrochloric acid, or of an organic acid such as, for example, oxalic acid, are reacted with enaminones of the formula (XVII)

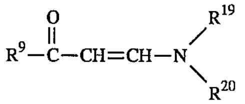

(XVII)

in which $R^9$ has the abovementioned meaning and $R^{19}$ and $R^{20}$ are identical or different and preferably represent straight-chain or branched alkyl having 1 to 6 carbon atoms, in particular straight-chain or branched alkyl having 1 to 4 carbon atoms, if appropriate in the presence of a diluent such as, for example, methanol or ethanol, and if appropriate in the presence of a base such as, for example, sodium methanolate or sodium ethanolate, at temperatures between +20° C. and +200° C.

b) Nitrobenzene derivative,s of the general formula (XIII-b)

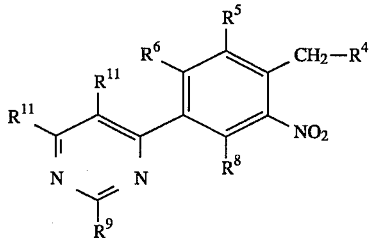

(XIII-b)

in which $R^4$, $R^5$, $R^6$, $R^8$, $R^9$, $R^{10}$ and $R^{11}$ have the abovementioned meanings, are obtained when compounds of the formula (XVIII)

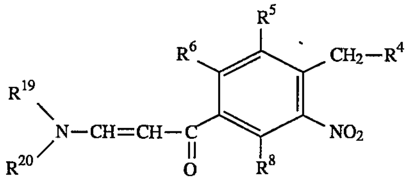

(XVIII)

in which $R^4$, $R^5$, $R^6$, $R^8$, $R^{19}$ and $R^{20}$ have the abovementioned meanings, are reacted with amidine derivatives of the formula (XIX)

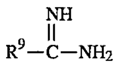

(XIX)

in which $R^9$ has the abovementioned meaning and

HX represents the equivalent of an inorganic acid such as, for example, hydrochloric acid, or of an organic acid such as, for example, oxalic acid, if appropriate in the presence of a diluent such as, for example, methanol or ethanol, and if appropriate in the presence of a base such as, for example, sodium methanolate or sodium ethanolate, at temperatures between +20° C. and +200° C.

c) The nitrobenzene derivatives of the general formulae (XIII-c), (XIII-d) and (XIII-e)

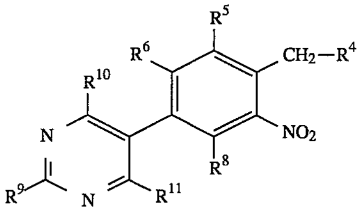

(XIII-c)

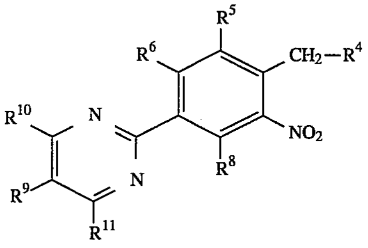

(XIII-d)

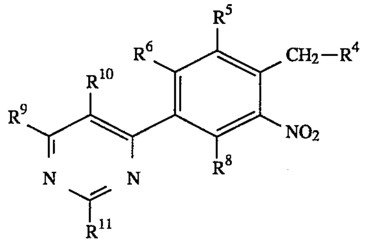

(XIII-e)

in which $R^4$, $R^5$, $R^6$, $R^8$, $R^9$, $R^{10}$ and $R^{11}$ have the abovementioned meanings, are obtained when nitrohalogenoaromatic compounds of the general formula (XX)

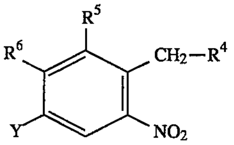

(XX)

in which $R^4$, $R^5$ and $R^6$ have the abovementioned meaning and

Y represents halogen, preferably bromine or iodine, are reacted either

α) with boronic acids of the formula (XXI)

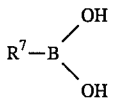

(XXI)

in which $R^7$ has the abovementioned meaning, or

β) with tin compounds of the formula (XXII)

$$R^7—Sn(R^{21})_3 \quad (XXII)$$

in which $R^7$ has the abovementioned meaning and $R^{21}$ preferably represents straight-chain or branched alkyl having 1 to 6 carbon atoms, in particular straight-chain or branched alkyl having 1 to 4 carbon atoms, in a known manner (cf. Nachr. Chem. Tech. Lab. 36, 1324 (1958) in a two-phase reaction in the presence of a diluent such as, for example, benzene or toluene, and in the presence of a base such as, for example, aqueous sodium carbonate solution or sodium hydrogen carbonate solution, and in the presence of a catalyst such as, for example, tetrakisphenylphosphine-palladium (O)', palladium dichloride/triphenylphosphine or bis-(triphenylphosphine)palladium dichloride, at temperatures between +20° C. and +200° C.

The compounds of the formula (XVI) and the amidine derivatives of the formula (XIX) are known and/or can be prepared in analogy to known processes (cf. Houben-Weyl-Müller, "Methoden der organischen Chemie [Methods of Organic Chemistry]", vol. XI/2, p. 38 et seq., Thieme Verlag Stuttgart (1958)).

Enaminones of the formula (XVII) and compounds of the formula (XVIII) are known and/or can be prepared in analogy to known processes (cf. Chem. Ber. 97, 3397 (1964 )).

Boronic acids of the formula (XXI) are known and/or can be prepared in analogy to known processes (cf. Adv. Chem. Ser. 102 (1959)).

Tin compounds of the formula (XXII) are likewise known and/or may be prepared by known processes (cf. Tetrahedron Lett. 4407 (1986)).

Formulae (Va) and (Vb) provide general definitions of the formamides and their derivatives furthermore required as starting substances for carrying out process (b) according to the invention. In these formulae (Va) and (Vb), $R^{2-2}$ preferably represents dialkylamino having in each case 1 to 6, in particular 1 to 4, carbon atoms in the individual straight-chain or branched alkyl moieties. $R^{2-2}$ very particularly preferably represents dimethylamino or diethylamino.

$R^{13}$ and $R^{14}$ independently of One another preferably represent in each case straight-chain or branched alkoxy having 1 to 4 carbon atoms, in particular methoxy or ethoxy, or represent a dialkylamino radical having in each case 1 to 6, in particular 1 to 4, carbon atoms in the individual straight-chain or branched alkyl moieties.

The formamides of the formula (Va) and their derivatives of the formula (Vb) are generally known compounds of organic chemist.

Formula (VI) provides a general definition of the ketocarboxylic acid derivatives required as starting substances for carrying out process (c) according to the invention.

In this formula (VI), $R^1$, $R^3$, $R^4$, $R^5$, $R^6$, $R^7$ and $R^8$ preferably represent those radicals which have already been mentioned in connection with the description of the substances of the formula (I) according to the invention as being preferred for these substituents.

The ketocarboxylic acid derivatives of the formula (VI) are new and likewise a subject of the invention. However, they are obtained in analogy to known processes, for example by reacting oxalic esters of the formula (XXIII)

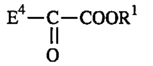

(XXIII)

in which $R^1$ has the abovementioned meaning and $E^4$ represents alkoxy or halogen, in particular methoxy, ethoxy or chlorine, with indole derivatives of the formula (XI)

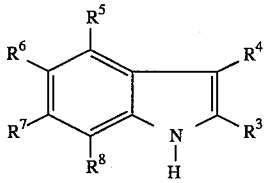

(XI)

in which $R^3$, $R^4$, $R^5$, $R^6$, $R^7$ and $R^8$ have the abovementioned meanings, if appropriate in the presence of a diluent such as, for example, dichloromethane or tetrahydrofuran, and if appropriate in the presence of a base such as, for example, n-butyllithium, sodium hydride, potassium t-butylate, triethylamine or pyridine, at temperatures between −80° C. and +80° C. (cf. DE-OS (German Published Specification) 3,807,232).

Formula (VII) provides a general definition of the organometallic compounds furthermore required as starting substances for carrying out process (c) according to the invention. In this formula (VII), $R^{2-3}$ preferably represents those radicals which have already been mentioned in connection with the description of the substances of the formula (I) according to the invention as being preferred for this substituent.

The organometallic compounds of the formula (VII) are known (cf., for example, J. Org. Chem. 33, 780 [68]; J. Org. Chem. 37, 939 [1972]).

Formula (VIII) provides a general definition of the substituted acrylic esters required as starting substances for carrying out process (d) according to the invention. In this formula (VIII), $R^1$, $R^3$, $R^4$, $R^5$, $R^6$, $R^7$ and $R^8$ preferably represent those radicals which have already been mentioned in connection with the description of the substances of the formula (I) according to the invention as being preferred for these substituents.

$E^2$ preferably represents a suitable acyloxy or sulphonyloxy radical, in particular an acetoxy, a methanesulphonyloxy or a p-toluenesulphonyloxy radical.

The substituted acrylic esters of the formula (VIII) were hitherto unknown.

They are obtained when hydroxyacrylic esters of the formula (II)

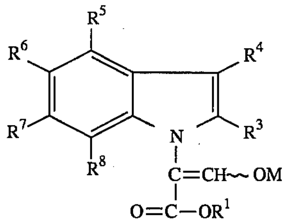

(II)

in which

M, $R^1$, $R^3$, $R^4$, $R^5$, $R^6$, $R^7$ and $R^8$ have the abovementioned meanings, are reacted with acid chlorides of the formula (XXIV)

$^{22}$—Cl (XXIV)

in which $R^{22}$ represents an acyl or sulphonyl radical, in particular an acetyl, a methanesulphonyl or a p-toluenesulphonyl radical, if appropriate in the presence of a diluent such as, for example, dichloromethane, and if appropriate in the presence of an acid-binding agent such as, for example, triethylamine or pyridine, at temperatures of from −20° C. to +120° C.

Acid chlorides of the formula (XXIV) are generally known compounds of organic chemistry.

Formula (IX) provides a general definition of the thiols furthermore required as starting substances for carrying out process (d) according to the invention. In this formula (IX), $R^{2-3}$ preferably represents those radicals which have already been mentioned in connection with the description of the substances of the formula (I) according to the invention as being preferred for this substituent.

The thiols of the formula (IX) are generally known compounds of organic chemistry.

Suitable diluents for carrying out process (a) according to the invention are inert organic solvents. These include, in particular, aliphatic, alicyclic or aromatic, optionally halogenated hydrocarbons such as, for example, benzine, benzene, toluene, xylene, chlorobenzene, petroleum ether, hexane, cyclohexane, dichloromethane, chloroform or carbon tetrachloride, ethers such as diethyl ether, dioxane, tetrahydrofuran or ethylene glycol dimethyl ether or ethylene glycol diethyl ether, nitriles such as acetonitrile or propionitrile, amides such as dimethylformamide, dimethylacetamide, n-methylformanilide, N-methylpyrrolidone or hexamethylphosphoric triamide, or sulphoxides such as dimethyl sulphoxide.

If appropriate, process (a) according to the invention can also be carried out in a two-phase system such as, for example, water/toluene or water/dichloromethane, if appropriate in the presence of a phase transfer catalyst. Examples of such catalysts which may be mentioned are: tetrabutylammonium iodide, tetrabutylammonium bromide, tributylmethylphosphonium bromide, trimethyl-$C_{13}/C_{15}$-alkylammonium chloride, dibenzyl-dimethyl-ammonium methylsulphate, dimethyl-$C_{12}/C_{14}$-alkylbenzylammonium chloride, tetrabutylammonium hydroxide, 15-crown-5, 18-crown-6, triethylbenzylammonium chloride, trimethylbenzylammonium chloride or tris-[2-(2-methoxyethoxy)-ethyl]-amine.

Process (a) according to the invention is preferably carried out in the presence of a suitable basic reaction auxiliary. Suitable reaction auxiliaries are all inorganic and organic bases which can customarily be used. The following are preferably used: alkali metal hydrides, alkali metal hydroxides, alkali metal amides, alkali metal alcoholates, alkali metal carbonates or alkali metal hydrogen carbonates such as, for example, sodium hydride, sodium amide, sodium hydroxide, sodium methylate, sodium ethylate, potassium t-butylate, sodium carbonate or sodium hydrogen carbonate, and also tertiary amines such as, for example, triethylamine, N,N-dimethylaniline, pyridine, N,N-dimethylaminopyridine, diazabicyclooctane (DABCO),$^{TM}$ diazabicyclononene (DBN) or diazabicycloundecene (DBU).

When carrying out process (a) according to the invention, the reaction temperatures can be varied within a substantial range. In general, the process is carried out at temperatures of from −30° C. to +120° C., preferably at temperatures of from −20° C. to +60° C.

For carrying out process (a) according to the invention, 1.0 to 10.0 moles, preferably 1.0 to 5.0 moles, of alkylating agent, of the formula (III) and, if appropriate, 1.0 to 5.0 moles, preferably 1.0 to 2.0 moles, of reaction auxiliary are generally employed per mole of 3-hydroxyacrylic ester or of a corresponding alkali metal salt of the formula (II). It is also possible in this context to prepare the 3-hydroxyacrylic esters or their alkali metal salts of the formula (II) which are required as starting compounds for carrying out process (a) according to the invention, directly in the reaction vessel in a preceding reaction and to further react them from the reaction mixture with the alkylating agent of the formula (III), without isolation, according to process (a) according to the invention ("one-pot process"). The reaction is carried out and the reaction products are worked up and isolated by generally customary methods (cf. also the preparation examples).

Suitable diluents for carrying out process (b) according to the invention are inert organic solvents. These include, in particular, aliphatic, alicyclic or aromatic, optionally halogenated hydrocarbons such as, for example, benzine, benzene, toluene, xylene, chlorobenzene, petroleum ether, hexane, cyclohexane, dichloromethane, chloroform or carbon tetrachloride, or ethers such as diethyl ether, dioxane, tetrahydrofuran or ethylene glycol dimethyl ether or ethylene glycol diethyl ether.

However, it is also possible to carry out process (b) according to the invention without adding a diluent.

When carrying out process (b) according to the invention, the reaction temperatures can be varied within a substantial range. In general, the process is carried out at temperatures of from −20° C. to +200° C., preferably at temperatures from 0° C. to 150° C.

For carrying out process (b) according to the invention, 1.0 to 30.0 moles, preferably 1.0 to 15.0 moles, of formamide of the formula (Va) or of a corresponding derivative of the formula (Vb) are generally employed per mole of substituted acetic ester of the formula (IV).

The reaction is carried out and the reaction products are worked up and isolated by generally customary methods (cf. in this context also G. Mathieu; J. Weill-Raynal "Formation of C-C Bonds", Vol. I; p. 229–244; Thieme Verlag Stuttgart 1973).

Suitable diluents for carrying out process (c) according to the invention are inert organic solvents. These include, in particular, aliphatic, alicyclic or aromatic hydrocarbons such as, for example, benzine, toluene, xylene, petroleum ether, hexane or cyclohexane, or ethers, such as diethyl ether, dioxane, tetrahydrofuran or ethylene glycol dimethyl ether or ethylene glycol diethyl ether.

When carrying out process (c) according to the invention, the reaction temperatures can be varied within a substantial range. In general, the process is carried out at temperatures of from −100° C. to +100° C., preferably at temperatures of from −80° C. to +50° C.

For carrying out process (c) according to the invention, 1.0 to 1.5 moles, preferably 1.0 to 1.2 moles, of organometallic compound of the formula (VII) are generally employed per mole of ketocarboxylic acid derivative of the formula (VI). The reaction is carried out and the reaction products are worked up and isolated by known processes (cf., for example, J. Org. Chem. 33, 780 [1968]; J. Org. Chem. 37, 939 [1972]).

Suitable diluents for carrying out process (d) according to the invention are inert organic solvents. These include, in particular, aliphatic, alicyclic or aromatic, optionally halogenated hydrocarbons such as, for example, benzine, benzene, toluene, xylene, chlorobenzene, petroleum ether, hexane, cyclohexane, dichloromethane, chloroform or carbon tetrachloride, ethers such as diethyl ether, dioxane, tetrahydrofuran or ethylene glycol dimethyl ether or ethylene glycol diethyl ether, ketones such as acetone or butanone, nitriles such as acetonitrile or propionitrile, amides such as dimethylformamide, dimethylacetamide, N-methylformanilide, N-methylpyrrolidone or hexamethylphosphoric triamide, esters such as ethyl acetate, or sulphoxides such as dimethyl sulphoxide.

Process (d) according to the invention is preferably carried out in the presence of a suitable reaction auxiliary. Suitable reaction auxiliaries are all customary inorganic or organic bases. These include, for example, alkali metal hydroxides such as sodium hydroxide or potassium hydroxide, alkali metal carbonates such as sodium carbonate, potassium carbonate or sodium hydrogen carbonate, or tertiary amines such as triethylamine, N,N-dimethylaniline, pyridine, N,N-dimethylaminopyridine, diazabicyclooctane (DABCO), diazabicyclononene (DBN) or diazabicycloundecene (DBU).

When carrying out process (d) according to the invention, the reaction temperatures can be varied within a substantial range. In general, the process is carried out at temperatures of from −20° C. to 180° C., preferably at temperatures of from 0° C. to 150° C.

If appropriate, the process according to the invention can also be carried out under pressure, depending on the boiling point of the reactants used, for example when low-boiling thiols of the formula (IX) are employed.

In this case, it is preferred to carry out the process under the pressure which is established under the reaction conditions when the mixture is heated to the reaction temperature required.

For carrying out process (d) according to the invention, 1.0 to 20.0 moles, preferably 1.0 to 5.0 moles, of thiol of the formula (IX) and, if appropriate, 1.0 to 5.0 moles, preferably 1.0 to 1.5 moles, of reaction auxiliary are generally employed per mole of substituted acrylic ester of the formula (VIII). The reaction is carried out and the reaction products are worked up and isolated by generally customary methods.

The active compounds of the formula (I) and of the formula (IV) according to the invention have a powerful action against pests and can be employed in practice for combating undesired harmful organisms. The active compounds are suitable for use as plant protection agents, in particular as fungicides or insecticides.

Fungicidal agents in plant protection are employed for combating Plasmoiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubensis;*
Plasmopara species, such as, for example, *Plasmopara viticola;*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus;*
Puccinia species, such as, for example, *Puccinia recondita;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae* and
Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds of the formulae (I) and (IV) according to the invention can be with particularly good success for protectively combating rice blast disease (*Pyricularia oryzae*) and plasmopara on vines. Moreover, the active compounds according to the invention have a very good fungicidal action against septoria nodorum, cochliobolus sativus, pyrenophora teres and fusarium nivale.

Moreover, the active compounds of the formulae (I) and (IV) according to the invention show an additional fungicidal action against Oomycetes, Venturia species on apples, Botrytis and *Pellicularia sasakii* on rice, and a broad and good in-vitro action.

In addition, the active compounds of the general formula (I) are suitable for combating animal pests, preferably arthropods and nematodes, in particular insects and arachnids, encountered in agriculture, in forestry, in the protection of stored products and of materials, and in the hygiene field.

They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea madeae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.*

From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodeco res spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphumavenae,* Myzus spp., *Phorodon humuli, Rhopalosiphum pad,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., Tenetrio molitor, Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp. From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The phytoparasitic nematodes include Pratylenchus spp., *Radopholus similis, Ditylenchus dipsaci, Tylenchulus semipenetrans,* Heterodera spp., Globedera ssp., Meloidogyne spp., Aphelenchoides spp., Longidorus spp., Xiphinema spp. and Trichodorus spp..

The active compounds of the formula (I) according to the invention are distinguished by an outstanding insecticidal activity, in particular when employed against beetle larvae such as, for example, *Phaedon choleariae, Plutella xylostella* and *Spodoptera frugiperda,* against cicadas such as, for example, Nephotettix, and against aphids such as, for example, *Myzus persicae,* and against spider mites such as, for example, *Tetranychus urticae.* The active compounds according to the invention furthermore have a very good ovicidal action.

Depending on their particular physical and/or chemical properties, the active compounds of the formulae (I) and (IV) can be converted to the customary formulations, such as solutions, emulsions, suspensions, powders, foams, pastes, granules, aerosols, natural and synthetic materials impregnated with active compound, very fine capsules in polymeric substances and in coating compositions for seed, and in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons, as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain 0.1 and 95 per cent by weight of active compound, preferably 0.5 to 90%.

The active compounds of the formulae (I) and (IV) according to the invention can be present in the formulations as a mixture with other known active compounds, such as fungicides, insecticides, acaricides and herbicides and as mixtures with fertilizers and growth regulators.

The active compounds of the formulae (I) and (IV) can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound preparation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

In the treatment of soil, active compound concentrations of 0.00001 to 0.1% by weight, preferably 0.0001 to 0.02% by weight, are required at the place of action.

Preparation Examples

Example 1

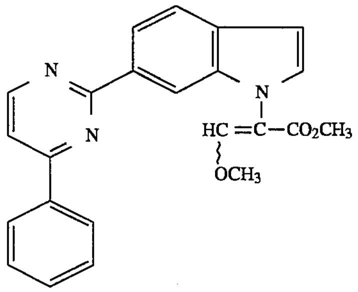

(Process (a)) ("one-pot" variant)

A mixture of 8.58 (25 mmol) of methyl[6-[4 -(phenyl)-pyrimidin-2-yl]-indol-1-yl]-acetate and 28.6 ml of methyl formate in 15 ml of dimethylformamide are slowly added dropwise at a temperature of 0° C. to 5° C. to a stirred and cooled suspension of 1.71 g (57 mmol) of sodium hydride (80% in paraffin) in 15 ml of dimethylformamide. Stirring at 0° C. is continued for 2 hours, and 7.5 ml (79 mmol) of dimethyl sulphate are then added at the same temperature to the vigorously stirred mixture. Stirring is continued for one hour, during which process the mixture is allowed to come to room temperature; excess saturated sodium hydrogen carbonate solution is then added to the reaction mixture, which is then extracted with ethyl acetate.

The combined organic phases are washed with water, dried over sodium sulphate and, after filtration, freed from solvent in vacuo. The residue is purified by column chromatography (eluent: petroleum ether/ethyl acetate 2:1).

7.5 g (78% of theory) of methyl 3-methoxy-2-[6 -[4-(phenyl)-pyrimidin-2-yl]-indol-1-yl]-acrylate are obtained as an E/Z isomer mixture of melting point 85° C.

Example 2

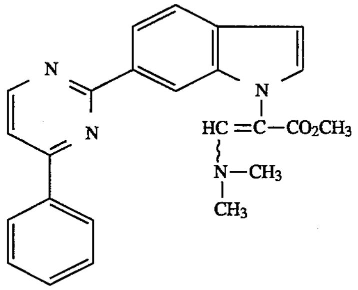

(Process (b))

A mixture of 1 g (2.9 mmol) of methyl [6-[4 -(phenyl)-pyrimidin-2-yl]-indol-1-yl]-acetate and 4 g of dimethylformamide dimethyl acetal is refluxed to the boil for 30 hours, with stirring. The mixture is allowed to cool and is concentrated, the residue is stirred with diisopropyl ether and the solid is filtered off with suction. The solid is washed with a little diisopropyl ether and dried.

1.1 g (95% of theory) of methyl 3-dimethylamino-2-[6-[4-(phenyl)-pyrimidin-2-yl]-indol-1-yl]-acrylate is obtained as an E/Z mixture of melting point 168° C.

The compounds of the formula (I) listed in Table 2 can be prepared analogously to Preparation Examples 1 and 2 and following the general instructions for processes (a), (b), (c) and (d) according to the invention.
TABLE 2
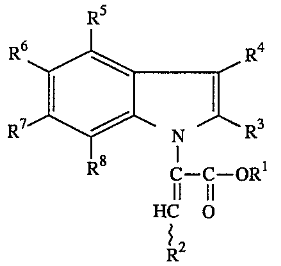
(I)
| Example No. | $R^1$ | $R^2$ | $R^3$ | $R^4$ | $R^5$ | $R^6$ | $R^7$ | $R^8$ | Melting point |
|---|---|---|---|---|---|---|---|---|---|
| 3 | $-CH_3$ | $-OCH_3$ | H | H | H | H | 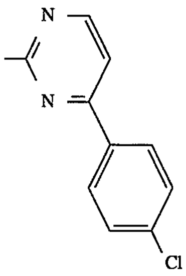 | H | *)95° C. |
| 4 | $-CH_3$ | $-OCH_3$ | H | H | H | H | 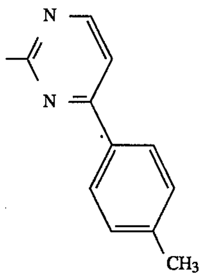 | H | *)90° C. |
| 5 | $-CH_3$ | $-OCH_3$ | H | H | H | H | 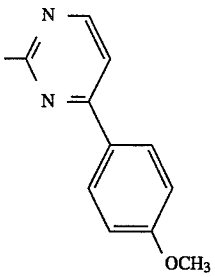 | H | *)90° C. |
| 6 | $-CH_3$ | $-OCH_3$ | H | H | H | H | 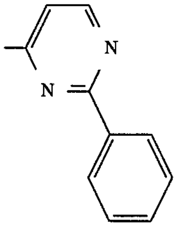 | H | *)95–97° C. |

TABLE 2-continued

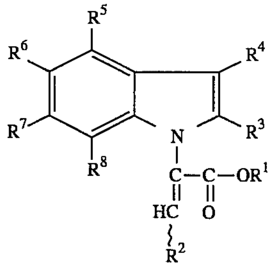

(I)

| Example No. | $R^1$ | $R^2$ | $R^3$ | $R^4$ | $R^5$ | $R^6$ | $R^7$ | $R^8$ | Melting point |
|---|---|---|---|---|---|---|---|---|---|
| 7 | $-CH_3$ | 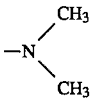 | H | H | H | H | 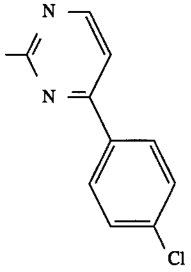 | H | *)168–172° C. |

*)E/Z isomer mixture

Preparation of the starting ,compounds

Example (IV-1)

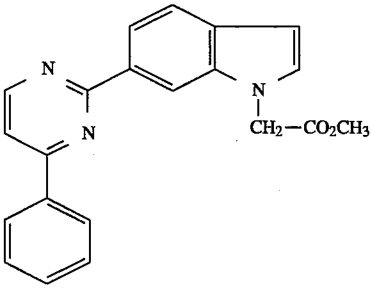

A mixture of 16.0 g (59 mmol) of 6-[4-(phenyl)pyrimidin-2-yl]-indole, 17.5 g (114 mmol) of methyl bromoacetate, 23.5 g of potassium carbonate and 130 ml of acetonitrile is refluxed to the boil for 6 hours, and the course of the reaction is monitored by means of thin-layer chromatography. When the reaction is complete, the mixture is allowed to cool and partitioned between water and ethyl acetate, and the organic phase is dried over sodium sulphate and concentrated. The residue is purified by column chromatography (eluent: petroleum ether/ethyl acetate 1:1).

12.9 g (53% of theory) of methyl[6-[4-(phenyl)pyrimidin-2-yl]-indol-1-yl]-acetate of melting point 111° C. are obtained.

The compounds of the formula (IV) listed in Table 3 can be obtained analogously to Preparation Example (IV-1).

TABLE 3
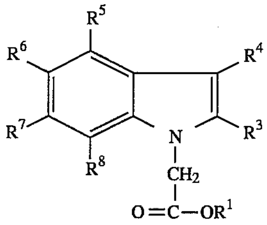
(IV)
| Example No. | $R^1$ | $R^3$ | $R^4$ | $R^5$ | $R^6$ | $R^7$ | $R^8$ | Melting point |
| --- | --- | --- | --- | --- | --- | --- | --- | --- |
| IV-2 | $-CH_3$ | H | H | H | H | 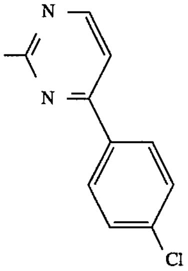 | H | 159° C. |
| IV-3 | $-CH_3$ | H | H | H | H | 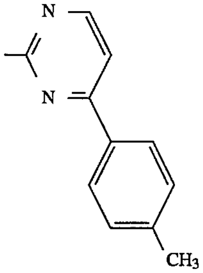 | H | 150° C. |
| IV-4 | $-CH_3$ | H | H | H | H | 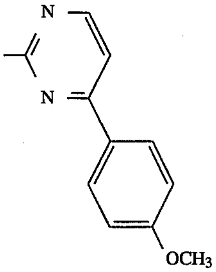 | H | 228° C. |
| IV-5 | $-CH_3$ | H | H | H | H | 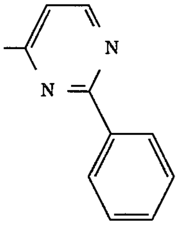 | H | 139° C. |

Example (XI-1)

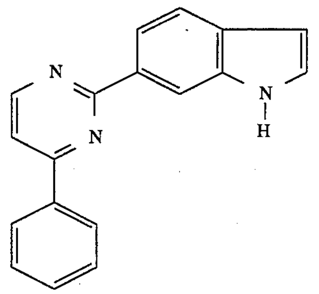

In an autoclave, a solution of 26.3 g (76 mmol) of β-dimethylamino-4-[4-(phenyl)-pyrimidin-2-yl]-2-nitrostyrene in 200 ml of tetrahydrofuran are hydrogenated for 5 hours at a hydrogen pressure of 50 bar and a temperature of 70° C., with the addition of 5 g of Raney nickel. The catalyst is separated off by filtration, the filtrate is concentrated, and the residue is purified by column chromatography (eluent: ethyl acetate).

19.8 g (66% of theory) of 6-[4-(phenyl)-pyrimidin-2-yl]-indole of melting point 160° C. are obtained.

The compounds of the formula (XI) listed in Table 4 can be obtained analogously to Preparation Example (XI-1).

TABLE 4

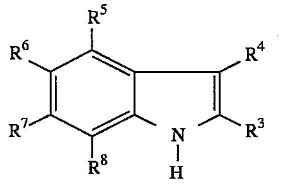

(XI)

| Example No. | $R^3$ | $R^4$ | $R^5$ | $R^6$ | $R^7$ | $R^8$ | Melting point |
|---|---|---|---|---|---|---|---|
| XI-2 | H | H | H | H | 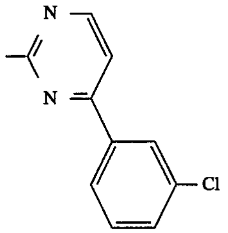 | H | 229° C. |
| XI-3 | H | H | H | H | 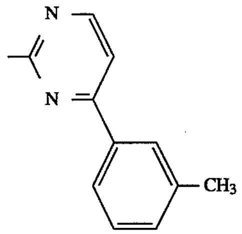 | H | 210° C. |
| XI-4 | H | H | H | H | 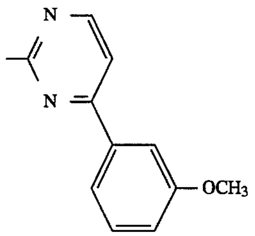 | H | 206° C. |

TABLE 4-continued

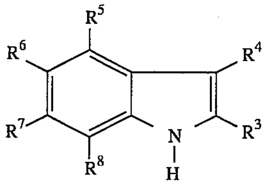

(XI)

| Example No. | $R^3$ | $R^4$ | $R^5$ | $R^6$ | $R^7$ | $R^8$ | Melting point |
|---|---|---|---|---|---|---|---|
| XI-5 | H | H | H | H | 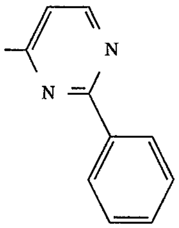 | H | Oil |

Example (XIII-1)

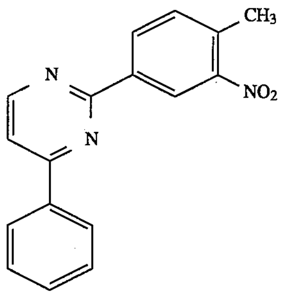

A mixture of 24.0 g (111 mmol) of 4-methyl-3 -nitro-benzamidine hydrochloride, 17.5 g (97 mmol) of 3 -dimethylamino-acryloylbenzene and 7.55 g (200 mmol) of sodium methanolate in 150 ml of ethanol is refluxed to the boil for 5 hours. After cooling, the reaction mixture is poured into ice-water, and the solid which has precipitated is filtered off with suction and dried.

20.0 g (79% of theory) of 2-methyl-5-(4 -phenyl-pyrimidin-2-yl)-nitrobenzene of melting point 139° C. are obtained.

The compounds of the formula (XIII) listed in Table 5 can be obtained analogously to Preparation Example (XIII-1) and taking into consideration the general instructions for the processes according to the invention.

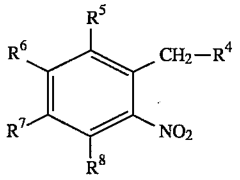

(XIII)

| Example No. | $R^4$ | $R^5$ | $R^6$ | $R^7$ | $R^8$ | Melting point |
|---|---|---|---|---|---|---|
| XIII-2 | H | H | H | 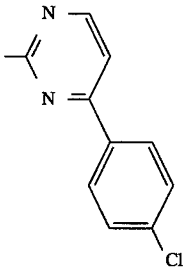 | H | 168° C. |
| XIII-3 | H | H | H | 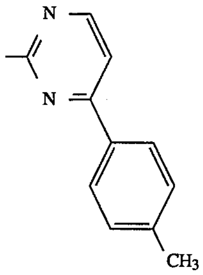 | H | 137° C. |
| XIII-4 | H | H | H | 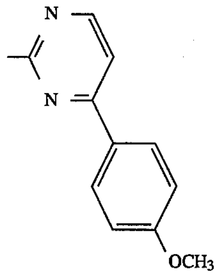 | H | 133° C. |

-continued (XIII)

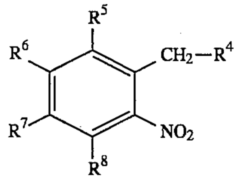

| Example No. | $R^4$ | $R^5$ | $R^6$ | $R^7$ | $R^8$ | Melting point |
|---|---|---|---|---|---|---|
| XIII-5 | H | H | H | 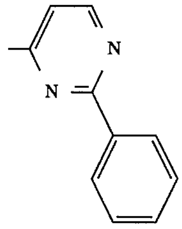 | H | 124° C. |

Example (XV-1)

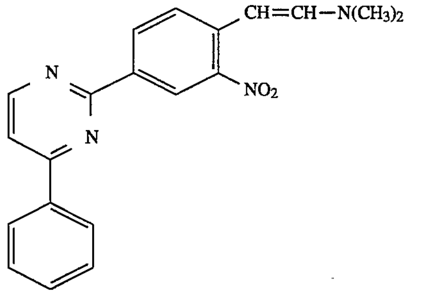

A mixture of 17.41 g (60 mmol) of 2-methyl-5-[4 -(phenyl)-pyrimidin-2-yl ]-nitrobenzene, 52 ml of dimethylformamide dimethyl acetal and 70 ml of dimethylformamide is refluxed to the boil for 12 to 20 hours until the reaction is complete (thin-layer chromatographic check). The mixture is then concentrated under greatly reduced pressure. The black-red residue, which is oily or crystalline, is further processed without further purification.

β-Dimethylamino-4-[4-(phenyl)-pyrimidin-2-yl ]-2-nitrostyrene is obtained as an oil.

The compounds of the formula (XV) listed in 1.5 Table 6 can be obtained analogously to Preparation Example ( XV-1) .

TABLE 6

(XV)

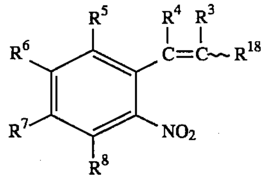

| Example No. | $R^3$ | $R^4$ | $R^5$ | $R^6$ | $R^7$ | $R^8$ | $R^{18}$ | Melting point |
|---|---|---|---|---|---|---|---|---|
| XV-2 | H | H | H | H | 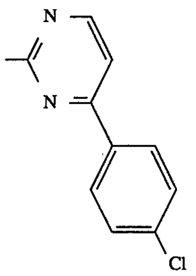 | H | 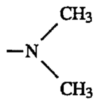 | 146° C. |

TABLE 6-continued

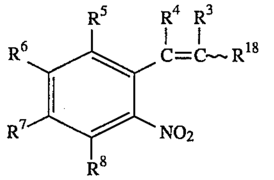

(XV)

| Example No. | $R^3$ | $R^4$ | $R^5$ | $R^6$ | $R^7$ | $R^8$ | $R^{18}$ | Melting point |
|---|---|---|---|---|---|---|---|---|
| XV-3 | H | H | H | H | 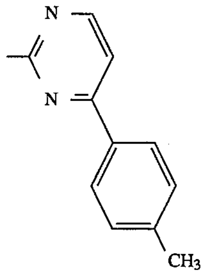 | H | 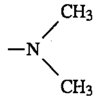 | 163° C. |
| XV-4 | H | H | H | H | 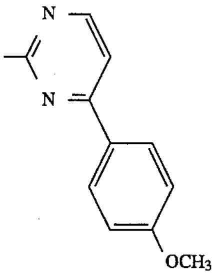 | H | 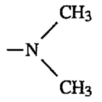 | Oil |
| XV-5 | H | H | H | H | 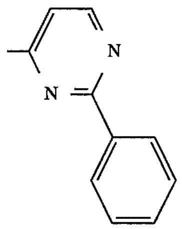 | H | 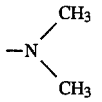 | Oil |

Use Examples

In the Use Examples which follow, the compound listed below was employed as comparison substance:

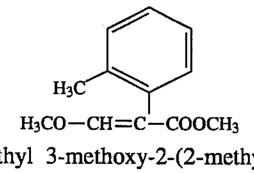

(A)

Methyl 3-methoxy-2-(2-methylphenyl)-acrylate (disclosed in EP-A 178,816).

Example A

Phaedon larvae test

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage plants (*Brassica oleracea*) are treated with the active compound preparation of the desired concentration. One leaf of the treated plants is placed in a plastic tin and infested with larvae ($L_3$) of the mustard beetle (*Phaedon cochleariae*). After 2 to 4 days, one more leaf from the same plant is used for each subsequent feeding.

After the desired periods of time, the destruction in % is determined. 100% means that all the beetles have been killed; 0% means that none of the beetles have been killed.

In this test, a superior activity compared with the prior art is shown, for example, by the following compounds oft he Preparation Examples: (1), (3), (4), (5) and (6).

Example B

Plutella test

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage plants (*Brassica oleracea*) are treated with the active compound preparation of the desired concentration. One leaf of the treated plants is placed in a plastic tin and infested with larvae ($L_2$) of the cabbage moth (*Plutella xylostella*). After 2 and 4 days, one more leaf from the same plant is used for each subsequent feeding.

After the desired periods of time, the destruction in % is determined. 100% means that all larvae have been killed; 0% means that none of the larvae have been killed.

In this test, a superior activity compared with the prior art is shown, for example, by the following compounds of the Preparation Examples: (1), (3), (4), (5) and (6).

Example C

Spodoptera test

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Soy bean plants (*Glycine soja*) are treated with the active compound preparation of the desired concentration. In ten replications, in each case one leaf of the treated plant is placed in a plastic tin and is infested with in each case one larva ($L_2$) of the armyworm (*Spodoptera frugiperda*). After 3 days, one further leaf of the corresponding plant is used for each tin for subsequent feeding. On day 7, the larvae are transferred to untreated artificial feed.

After the desired periods of time, the destruction in % is determined. 100% means that all larvae have been killed; 0% means that none of the larvae have been killed.

In this test, a superior activity compared with the prior art is shown, for example, by the following compounds of the Preparation Examples: (3) and (5).

Example D

Nephotettix test

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped in the active compound preparation of the desired concentration and infested with the green rice leafhopper (*Nephotettix cincticeps*) while the seedlings are still moist.

After the desired periods of time, the destruction in % is determined. 100% means that all cicadas have been killed; 0% means that none of the cicadas have been killed.

In this test, a superior activity compared with the prior art is shown, for example, by the following ccmpounds of the Preparation Examples: (3) and (5).

Example E

Myzus test

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Field bean plants (*Vicia faba*) which are infested with the green peach aphid (*Myzus persicae*) are treated by being dipped into an active compound preparation of the desired concentration.

After the desired periods of time, the destruction in % is determined. 100% means that all aphids have been killed; 0% means that none of the aphids have been killed.

In this test, a superior activity compared with the prior art is shown, for example, by the following ccmpounds of the Preparation Examples: (1), (3), (4) and (5).

Example F

Tetranychus test (OP resistant)

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with all development stages of the common spider mite or two-spotted mite (*Tetranychus urticae*) are treated by being dipped into the active compound preparation of the desired concentration.

After the desired periods, the destruction in % is determined. 100% means that all the spider mites have been killed; 0% means that none of the spider mites have been killed.

In this test, a superior activity compared with the prior art is shown, for example, by the following ccmpounds of the Preparation Examples: (3) and (5).

Example G

Ovicidal action on egg clusters of *Heliothis armigera* (cotton bollworm)

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Egg clusters on filter paper, aged 2 days, were immersed for 30 seconds in the active compound preparations of the desired concentration and, in sealed Petri dishes, deposited in the laboratory for 6 days under long-day conditions. The criterion for assessing the action was the percentage hatch inhibition compared with untreated egg clusters.

In this test, a superior activity compared with the prior art is shown, for example, by the following ccmpounds of the Preparation Examples: (1), (3) and (4).

Example H

Pyricularia test (rice)/protective

Solvent: 12.5 parts by weight of acetone

Emulsifier: 0.3 part by weight of alkylaryl polyglycol ether

To produce a suitable preparation of active compound, 1 part by weight of active compound is mixed with the stated amounts of solvent, and the concentrate is diluted with water and the stated amount of emulsifier to the desired concentration.

To test for protective activity, young rice plants are sprayed with the active compound preparation until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, clearly superior activity compared with the prior art is shown, for example, by the compound of Preparation Example (6).

It is understood that the specification and examples are illustrative but not limitative of the present invention and that other embodiments within the spirit and scope of the invention will suggest themselves to those skilled in the art.

We claim:

1. A substituted acetic acid ester of the formula

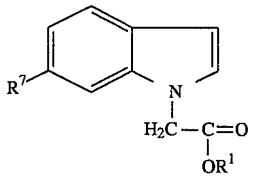

in which $R^1$ represents straight-chain or branched alkyl having 1 to 6 carbon atoms, $R^7$ represents

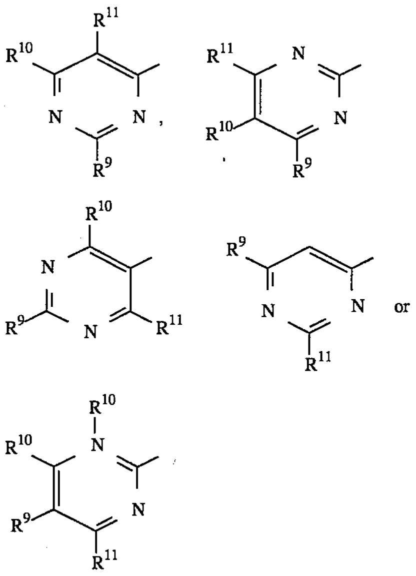

in which $R^9$, $R^{10}$, and $R^{11}$ represent phenyl, benzyl, phenoxy, phenylthio, benzyloxy, or benzylthio each of which is optionally substituted in the aryl moiety by identical or different substituents selected from the group consisting of fluorine, chlorine, bromine, $C_{1-4}$ alkyl, $C_{1-4}$ alkoxy, $C_{1-4}$ halogenoalkyl, and $C_{1-4}$ halogenoalkoxy.

2. A compound according to claim 1, wherein such compound is methyl[6-[4-(phenyl)-pyrimidin-2 -yl]-indol-1-yl]-acetate of the formula

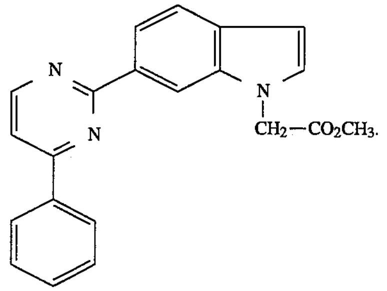

3. A compound according to claim 1, wherein such compound is methyl[6-[4-(4-chlorophenyl)pyrimidin-2-yl]-indol-1-yl]-acetate of the formula

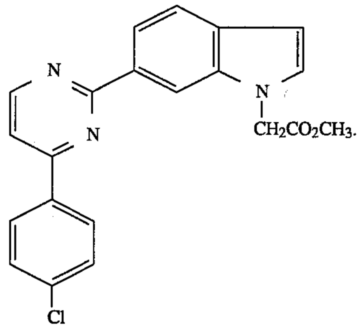

4. A compound according to claim 1, wherein such compound is methyl[6-[4-(4-tolyl)-pyrimidin-2 -yl]-indol-1-yl]-acetate of the formula

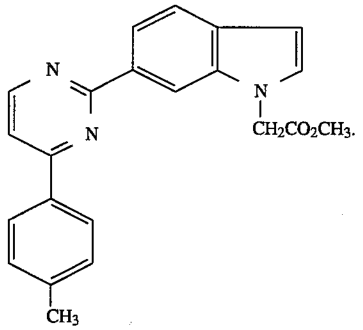

5. A compound according to claim 1, wherein such compound is methyl[6-[4-(4-methoxyphenyl)-pyrimidin-2-yl]-indol-1-yl]-acetate of the formula

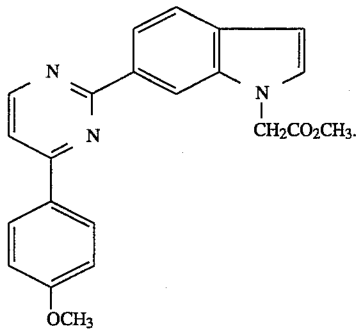

6. A compound according to claim 1, wherein such compound is methyl[6-[4-(phenyl)-pyrimidin-6-yl] -indol-1-yl]-acetate of the formula

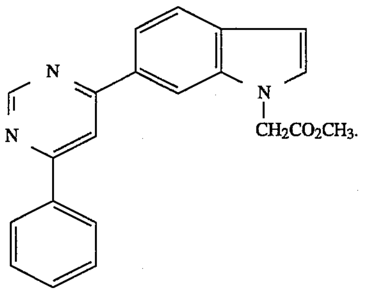

7. An insecticidal or fungicidal composition comprising an insecticidally or fungicidally effective amount of a compound according to claim 1 and a diluent.

8. A method of combating insects or fungi which comprises applying to such insects, fungus or a habitat thereof an insecticidally or fungicidally effective amount of a compound according to claim 1.

9. The method according to claim 8, wherein such compound is methyl[6-[4-(phenyl)-pyrimidin-2-yl]-indol-1-yl] -acetate, methyl[6-[4-(4-chlorophenyl)-pyrimidine-2-yl] -indol-1-yl] -acetate, methyl[6-[4-(4-tolyl)-pyrimidin-2-yl]-indol-1 -yl]-acetate, methyl[6-[4-(4-methoxyphenyl)-pyrimidin-2-yl)-indol-1-yl]-acetate, methyl[6-[4-(phenyl)-pyrimidin-6-yl]-indol-1-yl]-acetate.

* * * * *